United States Patent [19]

Lederer

[11] 4,013,513
[45] Mar. 22, 1977

[54] ION EXCHANGE CHROMATOGRAPHIC ISOENZYME SEPARATION AND ISOLATION

[75] Inventor: William H. Lederer, Pittsburgh, Pa.
[73] Assignee: E-C Apparatus Corporation, St. Petersburg, Fla.
[22] Filed: Jan. 30, 1976
[21] Appl. No.: 654,142
[52] U.S. Cl. .................... 195/66 R; 195/103.5 R
[51] Int. Cl.² ................ C07G 7/026; C12K 1/00
[58] Field of Search .................. 195/66 R, 103.5 R
[56] References Cited
OTHER PUBLICATIONS Nathan et al., Clinical Chemistry vol. 19, No. 9, pp. 1036–1039 (1973).
Nealon et al., Clinical Chemistry vol. 21, No. 3, pp. 392–397 (1975).
Mercer, Clinical Chemistry vol. 20, No. 1, pp. 36–40 (1974).

*Primary Examiner*—Lionel M. Shapiro
*Attorney, Agent, or Firm*—Sughrue, Rothwell, Mion, Zinn & Macpeak

[57] ABSTRACT

A process of separating and isolating fractions containing isoenzymes from a sample of tissue extract or blood serum comprising ion-exchange column chromatographically separating the sample containing the isoenzymes into a first fraction containing the hepatic isoenzyme of lactic acid dehydrogenase and a second fraction containing the myocardial isoenzymes of lactic acid dehydrogenase, the myocardial isoenzyme of creatine phosphokinase and prostatic acid phosphatase by ion-exchange column chromatographing the sample on a weakly-basic anion exchange chromatographic resin and sequentially eluting and collecting the first fraction and the second fraction.

22 Claims, No Drawings

ION EXCHANGE CHROMATOGRAPHIC ISOENZYME SEPARATION AND ISOLATION

BACKGROUND OF THE INVENTION

1. Field of the Invention

This invention relates to a process for separating isoenzymes from tissue extracts or blood sera using ion exchange chromatography. More specifically, this invention relates to a process for separating and isolating from tissue extracts or blood sera clinically significant isoenzymes, the level of which is useful in diagnosing hepatic, myocardial and prostatic disorders.

2. Description of the Prior Art

In disease of organs, various items specific for the tissue involved are emitted into the bloodstream. As a result, it has become routine diagnostic procedure to sample the blood to obtain a general profile of the health of many parts of the anatomy as opposed to doing exploratory surgery.

More specifically, it is well documented that the level of various enzymes is elevated in certain disease conditions. In particular, an increase in the level of lactic acid dehydrogenase (EC 1.1.1.27, hereinafter LDH for brevity) in blood serum occurs with myocardial infarction, liver disease, pulmonary disease, etc. Further, the level of the enzyme creatine phosphokinase (EC 2.7.3.2, hereinafter CPK for brevity) is elevated in the blood serum in a similar manner when myocardial infarction, as well as skeletal muscle trauma, muscular dystrophy, and other disorders occur. Also, an increase in the level of the enzyme acid phosphatase (EC 3.1.3.2, orthophosphoric monoester of phosphohydrolase (acid optimum), hereinafter AP for brevity) occurs due to disorders of the recticulo-endothelial system, of the blood and of the prostate gland.

In general, enzymes are present in multiple forms, with various forms being specific for certain organs. These multiple forms of the enzymes, generally called "isoenzymes", have the same function in each organ, have the same average molecular weight but differ in their molecular charges or differ in the degree of electrical charge. In the past, the identification of various isoenzymes has been accomplished by separating the various isoenzymes using electrophoresis on a supporting medium, such as a paper or gel medium.

With respect to LDH, clinically useful in diagnosing anatomical disorders, it has been found by electrophoretic analysis to exist in five multiple forms in blood sera. (See E. S. Vesell et al, *Proc. Soc. Exp. Biol. Med.*, 94, 96 (1957); T. Wieland et al, *Biochem. Z.*, 329, 112 (1957); F. Wroblewski et al, *Ann. N.Y. Acad. Sci.*, 94, 912 (1961); R. Richterich et al, *Clin. Chem. Acta*, 8, 178 (1963); and E. D. Wachsmuth et al, *Biochem. Z.*, 336, 545 (1963)). These five multiple forms are generally designated $LDH_1$, $LDH_2$, $LDH_4$ and $LDH_5$, with $LDH_1$ being the form which is most highly negatively charged and $LDH_5$ being the form which is least highly negatively charged, with the other forms varying in order in the degree of their electrical charge. By testing tissue extracts and blood sera and correlation of not only the level of but also the form of LDH, it has been found that LDH is specific for heart muscle and the level of $LDH_1$, and also of $LDH_2$, in blood sera is elevated in myocardial infarction as disclosed in C. R. Roe et al, *J. Lab. Clin. Med.*, 80, 577 (1972). In a similar manner, $LDH_5$ has been found to be specific for the liver and the level of $LDH_5$ is elevated in blood sera in hepatic disorders. (See R. J. Wieme et al, *Ann. N.Y. Acad. Sci.*, 94, 898 (1961); L. Cohen et al, *Med. Clin. N. Am.*, 50, 193 (1966); I. N. Ramdeo et al, *Am.J. Gastroenterol*, 55, 459 (1971); B. E. Sobel et al, *Circulation*, 45, 471 (1972)).

Electrophoretic analysis has also shown that CPK is present in three forms, CPK-MM, CPK-MB, and CPK-BB (as disclosed in D. M. Dawson et al, *Biochem. Biophys. Res. Comm.*, 21, 346 (1965)), with these three forms increasing in their negative charge respectively. It has been found that CPK-MM is found in skeletal muscle, heart and lung, CPK-MB is found mostly in the heart and CPK-BB is found mostly in the brain and the gastrointestinal tract. (See K. J. Van Der Veen et al, *Clin. Chem. Acta*, 13, 312 (1966)). With respect to these CPK isoenzyme forms, studies have shown that the level of CPK-MM is elevated in subjects with severe muscle trauma, while subjects with myocardial infarction have elevated levels of both CPK-MM and CPK-MB. (See C. R. Roe et al, supra, and K. K. Van Der Veen et al, supra)

Further, the analysis of AP has also shown that AP exists in multiple forms and one form, prostatic acid phosphatase (hereinafter PAP for brevity), is specific to diseases of the prostate gland. (See W. H. Fishman et al, *J. Biol. Chem.*, 200, 89 (1953), W. H. Fishman et al, *J. Clin. Invest.*, 32, 1034 (1953), L. T. Yam, *Am.J. Med.*, 56, 604 (1974) etc.).

In view of the diagnostic value, the importance of the isolation of and determination of the levels of various isoenzymes in tissue extracts and blood sera, for example, those described above, can be easily seen. Further, the necessity for substantially complete separation into the various forms for analysis is obviously quite important for diagnostic accuracy.

Accordingly, techniques whereby the various forms of isoenzymes, such as the isoenzymes described and discussed above, can be separated for meaningful diagnostic information are essential for use of such isoenzymes as diagnostic tools.

In the past, the classical procedure for identification of isoenzymes has been electrophoresis and in particular electrophoretic analysis and identification of CPK isoenzymes has been accomplished (see V. Anido et al, *Am.J. Clin.Pathol.*, 63, 761 (1974)). Unfortunately, electrophoretic analysis to identify isoenzymes involves a tedious, cumbersome and time-consuming method. Further, degradation or denaturation of the components present in the tissue extract or blood serum sample can occur, giving rise to erroneous results, due to problems inherent in the electrophoretic procedure.

To overcome the problems inherent in the electrophoretic method, ion exchange chromatography has been employed as a method for separation and isolation of isoenzymes and the use of ion-exchange chromatography has been shown to be a rapid and simple procedure for separation and isolation of isoenzymes.

While not desiring to be bound, the process of ion exchange chromatography is believed to utilize the molecular charge of the isoenzymes to bind the isoenzymes reversibly to an ion-exchange material with selective elution and collection then being possible according to the changes in the environment to which the ion-exchange material having the isoenzymes bound thereto is subjected. More specifically, the isoenzymes of LDH, CPK and AP are negatively charged and will bind to a weakly basic anion-exchange resin. In general, when ion-exchange chromatography is employed, a sample of blood serum or tissue extract containing the isoenzymes initially present is added to a column packed with the ion-exchange material. As the sample passes through the ion-exchange material in the chromatographic column, the isoenzymes, due to their negative charge, become bound to the ion-exchange resin at the active sites of the resin with the degree of bonding beind dependent upon the charge density. To recover the isoenzyme components present in a separate isoenzyme form, the isoenzymes bonded to the ion-exchange resin are eluted from the ion-exchange resin by changing the ionic strength and pH environment. A selective displacement of a certain isoenzyme or isoenzymes to the exclusion of others occurs. To recover the isoenzymes in a separated form, the ion-exchange resin is washed with different solutions of increasing ionic strength and decreasing pH, i.e., by washing the ion exchange resin successively with different salt solutions having increasing concentrations and decreasing pHs. Due to the successive increase in ionic strength a selective displacement of the isoenzymes in the order of their charge density occurs since their bonding strength to the ion-exchange resin is diminished due to the lower pH. As a result of this procedure, the most weakly negatively charged isoenzymes are eluted first and followed successively in order by an elution of or elutions of, depending upon the sequence of eluting solution additions, the more highly negatively charged isoenzymes which elute later. The change in the pH of the solution employed for elution gives rise to the ability to recover the more highly charged isoenzymes without the necessity to increase the ionic strength to a level at which the isoenzymes or the ion-exchange resin is destroyed.

Ion-exchange column chromatography has been employed in the past to separate both CPK and LDH isoenzymes into their individual isoenzyme forms. More specifically, K. Takahashi et al in *Clin. Chim. Acta*, 38, 285 (1972), describe a procedure whereby tissue extract and blood serum were subjected to a gradient elution in ion exchange chromatography using DEAE-Sephadex A-50 to obtain CPK isoenzymes. In this procedure, analysis was of 5 ml fractions using a total of 50 fractions to fractionate an initial 1 ml sample. The gradient elution in the ion exchange chromatography described was accomplished by using a salt gradient procedure employing a buffered sodium chloride solution of a concentration ranging from 0 to 0.5 M and a pH of 7.5. Unfortunately, the procedure described by Takahashi et al is tedious and time-consuming since such involves a gradient elution with multiple fractions being collected and analyzed for the presence of CPK isoenymes and, in fact, in many instances 50 different fractions were collected for analysis.

D. W. Mercer in *Clin. Chem.*, 20, 36 (1974) and ibid, 20, 895 (1974) and subsequent investigators (see M. A. Varat et al, *Circulation* 51, 855 (1975) and D. A. Nealon et al, *Clin. Chem.*, 21, 392 (1975)) disclose a technique involving step-wise or discontinuous ion-exchange chromatography for fractionation of CPK isoenzymes. The ion-exchange chromatography was accomplished on a DEAE-Sephadex A-50 ion-exchange resin filled in a chromatographic column utilizing a sample addition of blood sera followed by elution using a series of two or three elutants. In the Mercer procedure, buffered aqueous solutions of 0.1 molar and 0.2 molar sodium chloride, each with a pH of 8, were respectively used and, in some cases, a third elutant involving a buffered aqueous solution of 0.3 molar sodium chloride having a pH of 7.0 was employed. In the fractionation, the initial sample, generally 1 ml, was fractionated with multiple single 1 ml eluate fractions being collected. Each of these fractions was then assayed for CPK activity. This discontinuous ion-exchange chromatographic fractionation of CPK isoenzymes results in the production of some ten separate fractions, each of which has to be analyzed and assayed for CPK activity. The end results achieved in this discontinuous ion-exchange chromatographic procedure is a plot of assays of CPK activity for each of the fractions against fraction numbers. Again, as was the situation with the gradient technique of Takahashi et al, supra, analysis of a large number of fractions is required to use this method for CPK isoenzyme analysis.

Further, due to the difficulties in electrophoretic analysis, investigators such as L. E. Nathan et al, *Clin. Chem.*, 19, 1036 (1973) have evaluated and described techniques for ion-exchange chromatography on DEAE-Sephadex of LDH enzymes to obtain $LDH_5$ for assay as a diagnostic tool in hepatic disorders.

On examination of the prior art, of which the above is believed to be respresentative, it can be seen that while ion-exchange chromatographic separation is a definite advance over electrophoretic procedures, problems still exist relative to the prior art methods of separation and isolation of the clinically important CPK isoenzymes and LDH isoenzymes by ion-exchange chromatography in that, in these prior art methods, separation has been of the individual isoenzymes, generally involving a large number of samples which must be subsequently assayed for determination of the CPK and LDH isoenzyme levels, and, due to the inherent problems in the procedures described in the prior art, has resulted in the collection of fractions of various isoenzymes which need not be separated and collected for clinical evaluation, in particular of myocardial disorders. In addition, the procedures described in the prior art relative to the use of ion-exchange chromatography to separate CPK or LDH enzymes have resulted in, not only the production of multiple fractions, but have also resulted in excessive dilution of the eluates due to the nature of the sequential elution involved in the described procedures.

SUMMARY OF THE INVENTION

An object of this invention is to overcome the difficulties of the prior art procedures for the separation of isoenzymes.

Another object of this invention is to provide a process whereby clinically useful fractions of CPK and LDH isoenzymes as well as the PAP isoenzyme can be easily separated.

A further object of this invention is to provide a process whereby clinically important CPK isoenzymes, LDH isoenzymes and AP isoenzymes can be appropriately isolated and collected in fractions suitable for assay and diagnostic use.

An even further object of this invention is to provide a process for separation of isoenzymes present in tissue extracts or blood sera using ion-exchange chromatography to obtain one single fraction simultaneously containing the clinically important CPK-MB isoenzyme for diagnosis of myocardial disorders and also to obtain therein non-interfering $LDH_{1,2}$ and PAP isoenzymes which are clinically useful in confirmation of myocardial disorders and prostatic disorders, respectively.

An additional object of this invention is to provide an ion-exchange chromatographic method for obtaining from blood sera or tissue extracts two clinically useful fractions of the four isoenzymes, first $LDH_5$ and second CPK-MB, $LDH_{1,2}$ and PAP, of diagnostic value.

An even further object of this invention is to provide a process for separating blood sera and tissue extracts into fractions of clinically useful CPK, LDH and AP isoenzymes in a rapid manner with improved separation precision.

A still further object of this invention is to provide an ion-exchange chromatographic process for fractionation of blood sera and tissue extracts into isoenzymes in which the fractions obtained are diluted minimally and assay thereon can be accomplished without the necessity of concentration, although concentration of the fractions can be accomplished if desired, e.g. to obtain increased assay precision. Thus, if concentration is employed, concentration of only one single fraction containing CPK-MB, $LDH_{1,2}$ and PAP is necessary.

These and other objects are accomplished by the process of this invention described herein.

This invention provides a process of separating and isolating fractions containing isoenzymes from a sample of tissue extract or blood serum comprising ion-exchange column chromatographically separating a sample containing the isoenzymes into a first fraction containing the hepatic isoenzyme of lactic acid dehydrogenase ($LDH_5$) and a second fraction containing the myocardial isoenzymes of lactic acid dehydrogenase ($LDH_{1,2}$), the myocardial isoenzyme of creatine phosphokinase (CPK-MB) and prostatic acid phosphatase (PAP) by ion-exchange column chromatographing the sample on a weakly-basic anion-exchange chromatographic resin and sequentially eluting and collecting the first fraction and the second fraction, the chromatographing, eluting and collecting being conducted in accordance with the following sequence:

a. passing the blood serum or tissue extract sample through the anion-exchange resin, in a pre-swelled form, in a chromatographic column and collecting a first eluate passing through the column;

b. passing a first aqueous buffered salt solution through the anion-exchange resin in the chromatographic column and collecting a second eluate with the first eluate to obtain the first fraction containing the hepatic isoenzyme of lactic acid dehydrogenase ($LDH_5$), with the first aqueous buffered salt solution having a pH of about 7.0 to 8.5, containing a salt with an anion corresponding to the anion of the anion-exchange resin prior to passing the sample into the resin, having a concentration in terms of the anion of about 0.01 to 0.15 equivalent/liter and being passed in an amount such that up to about 3 volume equivalents, based on the sample, of the first aqueous buffered salt solution are passed;

c. sequentially passing a second aqueous buffered salt solution and a third aqueous buffered salt solution through the anion-exchange resin in the chromatographic column to obtain a third eluate, with the second aqueous buffered salt solution having a pH of about 7.0 to 8.5, containing a salt with an anion corresponding to the anion of the anion-exchange resin prior to the passing of the sample, having a concentration in terms of the anion of about 0.01 to 0.15 equivalent/liter and being passed in an amount such that at least about 4 volume equivalents, based on the sample, of the second aqueous buffered salt solution are passed, and with the third aqueous buffered salt solution having a pH of about 7.5 to 8.5, containing a salt with an anion corresponding to the anion of the anion-exchange resin prior to the passing of the sample, having a concentration in terms of the anion of about 0.15 to 0.25 equivalent/liter and being passed in an amount such that about 4 or less volume equivalents, based on the sample, of the third aqueous buffered salt solution are passed; and d. passing a fourth aqueous buffered salt solution through the anion-exchange resin in the chromatographic column and collecting a fourth eluate to obtain the second fraction containing the myocardial isoenzymes of lactic acid dehydrogenase ($LDH_{1,2}$), the myocardial isoenzyme of creatine phosphokinase (CPK-MB) and prostatic acid phosphatase (PAP), with the fourth aqueous buffered salt solution having a pH of about 6.5 to 7.5, containing a salt with an anion corresponding to the anion of the anion-exchange resin prior to the passing of the sample, having a concentration in terms of the anion of about 0.4 to 0.6 equivalent/liter and being passed in an amount such that about 1 to 6 volume equivalents, based on the sample, of the fourth aqueous buffered salt solution are passed.

Another embodiment of the process of this invention includes collecting only the second fraction produced in accordance with the process of this invention where the diagnostic interest is only in the isoenzymes contained in the second fraction separated.

DETAILED DESCRIPTION OF THE INVENTION

As will be described herein, this invention overcomes the difficulties experienced with the prior art methods described above by providing two single fractions, the first fraction containing the $LDH_5$ isoenzyme and the second fraction containing the CPK-MB isoenzyme as well as simultaneously providing the $LDH_{1,2}$ isoenzymes and prostate acid phosphatase PAP isoenzyme, each of which can be assayed in the same single second fraction. The process of this invention provides the ability to obtain discrete elution of the isoenzymes of interest, a fractionation of an initial sample of tissue extract or blood serum into two fractions having minimum dilution, which can be subsequently easily assayed according to standard techniques.

The invention also provides the ability to discard fractions which are unneeded for evaluation of a particular subject or to discard fractions which are diagnostically meaningless. In contrast to the prior art techniques, the present invention provides the ability to obtain one or two discrete fractions, minimally diluted, which can be easily assayed for those isoenzymes of particular diagnostic value in diagnosing hepatic disorders and/or myocardial disorders and/or prostatic disorders.

The process of this invention is described in detail below.

The samples of tissue extract (animal or human) or blood serum (animal or human) which are to be subjected to the process of this invention to provide the diagnostically important fraction(s) can be prepared or obtained using conventional techniques, for example, as disclosed in:

B. W. Moore et al, *General Biological Chemistry*, Vol. 235, Page 1359 (1960), M. S. Klein, *Cardiovascular Research*, 7, 412 (1973), R. Roberts et al, *Circulation*, 52, 743 (1973), *Fundamentals of Clinical Chemistry*, N. W. Tietz, Ed., W. B. Saunders Co., Philadelphia (1970).

In general, if a sample of tissue extract is to be employed in the process of this invention, the tissue of interest is macerated and homogenized in an appropriate medium such as an aqueous buffered salt solution, e.g., the first aqueous buffered salt solution used in the process of this invention as described hereinafter or a 0.25 M aqueous sucrose solution, subsequently centrifuged to remove solid particles and dialyzed, if necessary, and the supernatant obtained is employed as the sample. Where blood serum is to be used as the sample to be subjected to the process of this invention, in general, whole blood is collected using standard venipuncture techniques, collected without the presence of an anticoagulant and allowed to clot (generally about 10 to 30 minutes or possibly longer) and subsequently centrifuged to collect the serum as the supernatant. While hemolysis, if such occurs, does not affect the separation process of this invention, such should be avoided to obtain fractions with diagnostically meaningful levels of the isoenzymes of interest.

Once the initial sample is obtained, either a tissue extract or blood sera, this sample can be subjected to the process of this invention as follows.

A sample of the tissue extract or blood serum (hereinafter the terms "serum" and "sera" will be used collectively to describe both tissue extracts and blood sera prepared as described above) in used. The size of the sample which is initially employed can be varied somewhat but will of course be dependent upon the volume of the chromatographic column to be employed and the amount of, and capacity of the ion-exchange chromatographic resin employed therein, the sensitivity of the ultimate isoenzyme analysis method employed and similar procedural factors. Of course, a standard sample size, generally of about 0.1 to 2 ml, preferably 0.4 to 1.6 ml, more preferably 1 ml, is normally used since after assay, the level of the isoenzyme can be easily compared with standard isoenzyme levels previously correlated with clinical evaluations. The sample selected, with the sample size being recorded for subsequent adjustment on diagnosis, is simply added to a chromatographic column containing the ion-exchange resin to be used.

A suitable temperature range of about 2° to 45° C, preferably 20° to 35° C, can be employed. Unless hereinafter provided otherwise, the remaining steps in the process of this invention to be described subsequently can be suitably performed at these temperature ranges previously recited. Control of the temperature within these ranges is not an essential characteristic of the invention, but it should be recognized, again, to obtain meaningful assay values for diagnostic evaluation that degradation or denaturation of the components of the sample should not be allowed to occur due to use of excessively high temperatures. Similarly, excessively low temperatures should be avoided because of possible change in the anion-exchange resin. Further, the time after sample preparation and prior to initiation of the process of this invention is not an essential characteristic of this invention but again to avoid sample degradation and denaturation due to time, the time lapse between initial sample preparation and initiation of the process of this invention should be within about 2 to 3 days, preferably within about 24 hours.

The chromatographic column which is employed in the process of this invention and containing the ion-exchange resin can be of any general configuration suitable for column chromatography. A suitable column form would comprise a cylindrical column having a means for constriction toward the bottom of the column to retain the ion-exchange resin in the column and yet permit flow of liquid and a top portion, flared or enlarged, or which may accept a reservoir or other means for addition of the sample and eluting solution in the volumes used in the process of the invention, to facilitate initial sample addition and subsequent eluant solution addition. Substantially any suitable chromatographic column of any size and dimensions generally employed in column chromatography can be used in the process of this invention. Of course, the column diameter and dimensions would be appropriately set to achieve efficient separation and fractionation during chromatography and, in general, the length-to-inside diameter ratio can vary from about 3:1 to 10:1, preferably 4:1 to 5:1. Essentially, the only substantial requirement for the chromatographic column is that it have a volume sufficient to hold an appropriate amount of the ion-exchange resin and be capable of receiving the maximum solution volume, either initial sample or eluant solution, to be added during the course of the process of this invention. Suitable constrictions in the column which can be employed to retain the ion-exchange resin include a cotton plug, sintered glass, porous ceramic or polymer plugs, etc. Essentially any inert material which will not affect the sample, the eluant solution or the ion-exchange resin and yet will retain the ion-exchange resin and permit the flow of liquid solutions therethrough can be employed. As a specific example, it has been found that for solution volume, initial sample and eluant solutions, of 10 ml or less and using a diethylaminoethyl dextran anion-exchange resin that a column 70 mm long and 9 mm in inside diameter can be suitably employed, although these values are merely exemplary and are not to be considered as limiting. A 20 ml reservoir, e.g., for eluting solution addition, is suitable for use with the above column.

Suitable weakly-basic anion-exchange resins which can be employed in the process of this invention are weakly-basic anion-exchange resins such as diethylaminoethyl dextran (hereinafter DEAE-dextran) (DEAE-Sephadex A-50, a trade name produced by Pharmacia, Sweden) and diethylaminoethyl-cellulose, (hereinafter DEAE-Cellulose), commercially available and produced by Whattman and Bio-Rad. Other examples of ion-exchange resins which can be employed for the process of this invention include diethylaminoethyl argarose (hereinafter DEAE-argarose) (trade name Biogel A, produced by Bio-Rad), diethylaminoethyl acrylamide (hereinafter DEAE-acrylamide). DEAE-Sephadex A-50 is preferred for use in the process of this invention since such a resin has a suitable charge density, a suitable flow rate and the capability in which the column can be run to void of fluid and suitably the characteristics of such a diethylaminoethyl dextran resin include an ion-exchange capacity of about 0.5 to 5 meq/g and the resin is capable of passing materials having a molecular weight of about 30,000 to 200,000.

An appropriate amount of the anion-exchange resin pretreated in accordance with the following is then added to the chromatographic column and any liquid allowed to drain from the column. The amount of the anion-exchange resin which is employed will vary somewhat since the amount generally will be related to initial sample volume to be fractionated and eluant solution volume used but in general for an initial sample volume of about 1 ml and eluting solution volumes of 10 ml or less, an appropriate amount of the pretreated anion-exchange resin will range from about 40 to 140 mg, preferably 70 to 110 mg, for the DEAE-dextran resin (DEAE-Sephadex A-50), about 250 to 350 mg of the DEAE-cellulose resin, about 125 to 175 mg of the DEAE-argarose resin and about 125 to 175 mg of the DEAE-acrylamide resin. Where larger or smaller volumes of the initial sample are employed, appropriate adjustments in the amount of the ion-exchange resin amount can be easily made.

As described above, the ion-exchange resin is generally pretreated, e.g., by soaking the resin, to accomplish swelling and place the anion-exchange resin in the correct pH and ionic strength environment. For example, where diethylaminoethyl dextran (DEAE-Sephadex A-50) is employed, the pretreatment can be with an aqueous buffered salt solution containing an anion corresponding to the initial anion form of the anion-exchange resin and, where such is in the chloride form, an aqueous buffered salt solution of sodium chloride, potassium chloride, lithium chloride and other water-soluble chlorides, preferably sodium chloride or potassium chloride, most preferably sodium chloride, having a pH ranging from about 7.0 to 8.5, preferably 7.95 to 8.05 is used. Preferably the first aqueous buffered salt solution used in the process of this invention is used for pretreatment. The buffering of the aqueous chloride solution can be achieved by using any cationic buffer such as tris(hydroxymethyl)aminomethane/HCl (Tris/HCl), or an alkylamine, aminoethyl alcohol, ammonia, barbitol at a pH below 7.5, ethylenediamine, imidazole, pyridine, etc. A suitable buffer concentration can range from about 0.01 to 0.1 molar, with 0.05 molar Tris/HCl buffer being preferred. The other anion-exchange resins suitable for use in this invention are appropriately pretreated in a similar manner.

Once the fines have been removed from the pretreated anion-exchange resin and such has been added to the chromatographic column, an amount of aqueous pretreatment solution, for example, as described above, i.e., an aqueous buffered sodium chloride solution having the same pH, e.g., of about 7.0 to 8.5, preferably 7.95 to 8.05, as the chloride solution used for pretreatment, is added to the chromatographic column containing the anion-exchange resin and the column then is allowed to drain of any excess solution. Alternatively, an aqueous buffered potassium chloride or lithium chloride solution of similar characteristics could be used for the aqueous buffered sodium chloride solution, if desired. For simplicity, an aqueous solution of similar characteristics using the same salt is employed, e.g., where an aqueous buffered sodium chloride solution is used for pretreatment, a similar aqueous buffered sodium chloride solution would be used.

As described above, a sample, i.e., an aliquot of the serum, is added to the top of the column and the eluate passing through the resin in the column after the addition of the sample is collected. A suitable time elapsed from the addition of the sample to the column and the collection of subtantially all of the first eluate generally is around 2 to 3 minutes for a DEAE-dextran resin, with collection of substantially all of the eluate being obtained when the DEAE-dextran resin-filled column stops dripping.

Following the addition of the sample to the top of the chromatographic column and the collection of the eluate obtained, a first aqueous buffered salt solution is then passed through the anion-exchange resin in the chromatographic column and a second eluate together with the first eluate obtained from the sample addition alone is collected, e.g., in the same collector, to obtain a first isoenzyme-containing fraction. This first fraction collected comprising the eluate of the sample alone and that obtained after the addition of the first aqueous buffered salt solution includes the $LDH_5$ isoenzyme. A suitable time period elapsed for collecting the second eluate with the first eluate is around 2 to 3 minutes. Again elution completion can be monitored as described above.

To obtain this second eluate, the first aqueous buffered salt solution employed has a pH ranging from about 7.0 to 8.5, preferably 7.95 to 8.05, and is an aqueous solution of a salt in which the anion of the salt is an anion corresponding to the anion of the anion-exchange resin employed prior to passage of the sample into the chromatographic column. More specifically, where DEAE-Sephadex A-50 is employed, an aqueous buffered solution of a chloride can be used, the chloride in the first aqueous buffered salt solution corresponding to the chloride form of the anion-exchange resin prior to passage of the sample therethrough. The pH of the first aqueous buffered salt solution having the pH range described hereinbefore can be achieved by the addition of any cationic buffer solution as hereinbefore described.

This first aqueous buffered salt solution is passed through the anion-exchange resin in order to completely elute the $LDH_5$ isoenzyme and accordingly, an appropriate concentration of the anion needed to accomplish the selective elution of the $LDH_5$ isoenzyme to the exclusion of the other isoenzyme components present ranges from about 0.01 to 0.15 equivalents per liter, preferably 0.09 to 0.11 equivalents per liter, in terms of the anion.

The amount of the first aqueous buffered salt solution passed through the anion-exchange resin will of course depend upon the initial sample volume employed with a larger volume of the first aqueous buffered salt solution being passed with a larger volume of the initial sample employed. In general, the volume of the first aqueous buffered salt solution which can be suitably employed in the process of this invention is an amount such that up to about 3 volume equivalents, e.g., about 0.1 to about 3 volume equivalents, preferably 0.9 to 1.1 volume equivalents, of the first aqueous buffered salt based on the volume of the initial sample is passed. What is important to control in the elution to obtain the first eluate after the initial sample addition is the interrelationship between not only the pH of the first aqueous buffered salt solution employed but also the concentration of the first aqueous buffered salt solution employed and the volume of the first aqueous buffered salt solution employed since to achieve a proper and definite elution, these parameters should be controlled as described above. Variation in initial sample size and correspondingly the amount of the first aqueous buffered salt solution passed can occur as long as the appropriate interrelationship described above between the amount of the initial sample and the amount of the first aqueous buffered salt solution having the recited pH and concentration is maintained.

As described above, the first eluate obtained upon simply passing the sample through the anion-exchange resin in the chromatographic column is collected and subsequently combined with the eluate obtained by passing the first aqueous buffered salt solution through the anion-exchange resin as described above to achieve the first fraction containing the LDH$_5$ isoenzyme. Depending upon the diagnostic interest, analysis of this combined eluate for LDH$_5$ activity, in accordance with well-recognized procedures known in the art, for example, as disclosed in W. E. C. Wacker et al, *New Eng. J. Med.*, 255, 449 (1956). Alternatively, if an assay of the LDH$_5$ activity is not of diagnostic interest, then this combination of eluates as the first fraction can be discarded. Alternatively, as described hereinafter with respect to a second embodiment of this invention, the first aqueous buffered salt solution and second aqueous buffered salt solution (described hereinafter) can be combined and passed through the anion-exchange resin in the chromatographic column, with the eluates after addition of the sample and of the first and second aqueous buffered salt solutions being discarded.

After the first aqueous buffered salt solution is passed through the anion-exchange resin in the column to obtain the first fraction as described above, a second aqueous buffered salt solution and a third aqueous buffered salt solution are sequentially passed through the anion-exchange resin in the chromatographic column to obtain a third eluate. This third eluate generally is not of any meaningful diagnostic value and accordingly can be discarded, similar to the discarding which would occur if analysis and assay of LDH$_5$ activity were not of diagnostic interest.

The second aqueous buffered salt solution and the third aqueous buffered salt solution passed through the anion-exchange resin in the chromatographic column are employed to remove diagnostically unnecessary isoenzyme forms and proteins still bound to the active sites of the ion-exchange resin and to convert the system into a system from which the second fraction containing the diagnostically important isoenzymes can be eluted rapidly and in a small volume in the last step of the process of this invention.

Similar to the first aqueous buffered salt solution employed, the second and third aqueous buffered salt solutions have appropriate concentrations and pHs and are used in appropriate minimum volumes, depending upon the initial sample size, to accomplish the elution of these diagnostically unnecessary isoenzyme forms. More specifically, the second aqueous buffered salt solution can be an aqueous buffered solution of a salt with an anion corresponding to the anion of the anion-exchange resin prior to the passing of the initial sample. Suitable examples of such salts include those salts hereinbefore described for the first aqueous buffered salt solution. A suitable pH for the second aqueous buffered salt solution can range from about 7.0 to 8.5, preferably 7.95 to 8.05, with this pH being achieved by use of a buffer system such as a cationic buffer system as described hereinbefore for the first aqueous buffered salt solution.

The second aqueous buffered salt solution, as described above, contains a salt with an anion corresponding to the anion of the anion-exchange resin prior to the passing of the initial sample with the anion being present at a concentration in terms of the anion of about 0.01 to 0.15 equivalents per liter, preferably 0.09 to 0.11 equivalents per liter and the second aqueous buffered salt solution is passed in such amount that at least about 4 volume equivalents, e.g., about 4 volume equivalents to about 10 volume equivalents, based on the volume of the initial sample, of the second aqueous buffered salt solution are passed.

The third aqueous buffered salt solution which is passed through the anion-exchange resin in the chromatographic column, in general, has the same type of characteristics that the second aqueous buffered salt solution has but differs in terms of the concentration and the amount of solution passed. More specifically, a suitable pH for the third aqueous buffered salt solution can range from about 7.5 to 8.5, preferably 7.95 to 8.05, and can be achieved using the same salts and by buffering in the same manner as described above for the second aqueous buffered salt solution using similar cationic buffer materials as described above. Further, the concentration of the salt containing the anion corresponding to the anion of the anion-exchange resin prior to the passing of the sample, can range from about 0.15 to 0.25 equivalent/liter, preferably 0.19 to 0.21 equivalent/liter, in terms of the anion and with the amount of the third aqueous buffered salt solution passed being such that about 4 or less volume equivalents, e.g., about 0.1 to 4 volume equivalents, preferably 1.9 to 2.1 volume equivalents, based on the sample, of the third aqueous buffered salt solution are passed.

The eluates obtained upon passing the second aqueous buffered salt solution and the third aqueous buffered salt solution, as described above, collected either separately or together, in general is discarded since they contain diagnostically meaningless isoenzyme forms. In general, suitable elution has occured with the passing of both the second aqueous buffered salt solution and the third aqueous buffered salt solution in about 15 minutes. Monitoring of elution completion can be as described hereinbefore.

In the last step of the process of this invention in which a fourth aqueous buffered salt solution is passed through the anion-exchange resin in the chromatographic column, a second fraction containing isoenzyme forms of diagnostic interest is obtained. This fourth aqueous buffered salt solution is simply added to the chromatographic column and allowed to pass through the anion-exchange resin with the eluate obtained being collected for subsequent assay. This eluate collected after passage of the fourth aqueous buffered salt solution is the second fraction containing isoenzymes of diagnostic interest and includes in the single fraction the LDH$_{1,2}$, CPK-MB and prostatic acid phosphatase isoenzymes which can be assayed in the normal manner as described in, e.g., W. E. C. Wacker et al, supra; S. B. Rosalki, *J. Lab. Clin. Med.*, 69, 696 (1967); and A. V. Roy et al, *Clin. Chem.*, 17, 1093 (1971); M. A. Andersch et al, *Amer. J. Clin. Path.*, 17, 571 (1947).

Again, as was the situation with the first, second and third aqueous buffered salt solutions, the fourth aqueous buffered salt solution has an appropriate pH, contains an appropriate anion, has an appropriate concentration and is passed in such a volume to achieve elution of the above-described isoenzymes of diagnostic interest. A suitable pH for the fourth aqueous buffered salt solution is a pH of about 6.5 to 7.5, preferably 6.95 to 7.05. The fourth aqueous buffered salt solution is a buffered solution and also contains a salt with an anion corresponding to the anion of the anion-exchange resin prior to the passing of the sample. Suitable examples of salts and buffers which can be employed include those salts and cationic buffers hereinbefore described. The fourth aqueous buffered salt solution containing the anion as described above has a concentration, in terms of the anion of about 0.4 to 0.6 equivalent/liter, preferably 0.5 to 0.6 equivalent/liter, and is passed through the anion-exchange resin in the chromatographic column in such an amount that about 1 to 6 volume equivalents, preferably 1.9 to 2.1 volume equivalents, based on the sample of the fourth aqueous buffered salt solution are passed in order to elute the diagnostically important isoenzymes discussed above as the second fraction. Suitable elution times for eluting these bound isoenzymes is generally within about 5 minutes and monitoring of elution completion can be as hereinbefore described.

As can be seen from the above, this embodiment of the process of this invention provides a rapid method to obtain a separation into two fractions containing isoenzymes of diagnostic interest, the overall process in general taking only about 30 to 35 minutes.

Further, with respect to the aqueous solutions employed, generally water is used as a medium for the salt and the buffer but appropriate compatible materials which do not effect the sample or anion-exchange resin, such as appropriate preservatives, e.g., antimicrobials, can additionally be present. Materials such as alcohols should be avoided because of a denaturation of the isoenzymes being separated.

Further, the process of this invention is easy to conduct and time elapsed between the steps is not of any concern to the operation but excessive time lapse should be avoided to prevent degradation and denaturation of the isoenzymes and to obtain meaningful isoenzyme assay values. Where some time lapse is unavoidable, storage of sample, the column containing the bound isoenzymes or the fractions eluted in a refrigerator is suitable to minimize change and denaturation of the materials.

In order to further describe the invention in greater detail, the following general example of the use of the above embodiment of the process of this invention is given without intending to limit the process thereto.

As described above, as an initial sample, the blood of a subject (animal or human) is collected without an anticoagulant and is allowed to clot. After clotting, the blood is centrifuged to collect the resulting supernatant, the serum, generally without allowing hemolysis to occur. Alternatively, if tissue (animal or human) extract is to be employed, the tissue is extracted with an appropriate medium, centrifuged to remove solid material, and ultimately the supernatant is obtained.

A chromatographic column, for example, 70 mm long and 9 mm in inside diameter, with a porous cotton plug constricting the lower output end to retain the resin yet permit the liquid drainage and with a flared upper input end is used and the column is filled with 90 mg of preswelled diethylaminoethyl dextran (DEAE-Sephadex A-50) (in a 0.1 molar sodium chloride aqueous solution buffered with 0.05 molar Tris/HCl to a pH of 8) and 5.25 ml of buffered 0.01 molar sodium chloride, having a pH of 8.0, buffered with 0.05 molar Tris/HCl with the lower end of the chromatographic column capped. Prior to the addition of the initial serum sample, 2 ml of 0.1 molar sodium chloride having a pH of 8.0 buffered with 0.05 molar Tris/HCl is added and the column is allowed to drain.

A 1 ml aliquot of the serum is added to the top of the chromatographic column and the eluate (first eluate) obtained after this addition is collected. Then 1 ml of 0.1 molar sodium chloride, having a pH of 8.0 buffered with 0.05 molar Tris/HCl (first aqueous buffered salt solution) is added and the eluate (second eluate) collected with the serum eluate previously collected. This combined eluate (first fraction) comprises the first fraction which contains the hepatic lactic acid dehydrogenase, $LDH_5$, which can be assayed in a conventional manner as described above. Where elevated levels of $LDH_5$ are found, this can be evidence of liver disease.

Next, 7 ml of 0.1 molar sodium chloride having a pH of 8.0, buffered with 0.05 molar Tris/HCl (second aqueous buffered salt solution) is passed through the column. Subsequently, in a similar manner, 2 ml of 0.2 molar sodium chloride, having a pH of 8.0, buffered with 0.05 molar Tris/HCl (third aqueous buffered salt solution) is passed through the column and the eluate (third eluate) obtained is discarded. This allows removal of isoenzymes which are of no diagnostic interest.

Then, 2 ml of 0.5 molar sodium chloride, having a pH of 7.0, buffered with 0.05 molar Tris/HCl, (fourth aqueous buffered salt solution) is passed through the chromatographic column and this eluate (second fraction) collected. The eluate collected comprises the second fraction and contains simultaneously the diagnostically valuable $LDH_{1,2}$, CPK-MB, and PAP isoenzymes in a single fraction. These isoenzymes can then be assayed in a normal manner as described above.

In a second embodiment of the process of this invention, the process can be conducted as described above except that the first eluate obtained from the sample is discarded. Then the second aqueous buffered salt solution is combined with the first aqueous buffered salt solution as a combination, with the volume used being adjusted upward, and the combination is passed through the anion-exchange resin prior to passing the third aqueous buffered salt solution, with the eluate also obtained as a result being discarded. Then the fourth aqueous buffered salt solution is then passed through the anion exchange resin and the eluate containing the myocardial isoenzymes of lactic acid dehydrogenase ($LDH_{1,2}$), the myocardial isoenzyme of creatine phosphokinase (CPK-MB) and prostatic acid phosphatase (PAP) is collected and assayed as described for the first embodiment hereinbefore described. Such an embodiment can be employed where diagnostic interest is in the myocardial isoenzymes or in prostatic acid phosphatase.

The second embodiment of this invention can in general be performed using the above-described specific procedure for the first embodiment of this invention, but with such being altered by adding 8 ml of a 0.1 molar sodium chloride aqueous solution having a pH of 8.0, buffered with 0.05 molar Tris/ HCl, rather than the 1 ml and 7 ml volume increments previously described as being used, and discarding all eluates obtained except for the eluate obtained on addition of the 0.5 molar sodium chloride aqueous solution as the last step of the above-described procedure.

From the examination of the disclosure set forth above, it can be seen that the process of this invention provides the ability to separate and isolate two isoenzyme-containing fractions, the analysis of which can give rise to a wealth of diagnostic data. Of considerable importance in evaluating the myocardial isoenzymes is the presence of both CPK-MB and $LDH_{1,2}$, which are considered of significant diagnostic value, in the same eluate or fraction. For example, if the CPK-MB is nondetectable, upon assay, either due to use of an insensitive assay procedure or absence because a myocardial infarction has not occurred or the blood of the subject was sampled late (e.g., 2 to 3 days post infarction), the $LDH_{1,2}$ assay provides confirmation of the proper working of the procedure since the normal values are within normal sensitivities of assays of $LDH_{1,2}$ or the $LDH_{1,2}$ value provides diagnostic information.

Further, since the fractions obtained are small, minimal dilution of the fraction occurs and the necessity for concentration of the fractions before assay is eliminated. However, if further sensitivity of the assay of the individual fractions is desired, each of the two fractions isolated according to the process of this invention as described above can be concentrated using conventional techniques and procedures. Of course, it will be readily apparent that concentration of the two single important fractions, either or both, by the process of this invention, is more beneficial than concentrating the original sample prior to analysis. Further, the salt employed to elute, the concentration of the salt employed and the pH employed for the eluant do not affect the assay technique nor do they affect the assay technique if the fraction to be analyzed is concentrated.

The following non-limiting examples of the invention are given for the purposes of exemplification of the invention. Unless otherwise indicated, all parts, percents, ratios and the like are by weight. Further, unless otherwise indicated, all procedures were conducted at atmospheric pressure and at a temperature of about 25° C.

EXAMPLE 1

Blood is drawn by standard venipuncture techniques. No anticoagulants are used and the cells are separated from the serum supernatent as soon as adequate clot formation has occurred. The serum sample is stored in a well washed container because of the possibility of contamination.

A chromatographic column, 70 mm long and 9 mm in inside diameter, with a porous cotton plug constricting the lower output end to retain the resin yet permit liquid drainage and with a flared upper input end is used and the column is filled with 90 mg of preswelled diethylaminoethyl dextran (DEAE-Sephadex A-50) (in a 0.1 molar sodium chloride aqueous solution buffered with 0.05 molar Tris/HCl) with the lower end of the chromatographic column capped. Prior to the addition of the initial serum sample, 2 ml of 0.1 molar sodium chloride having a pH of 8.0 buffered with 0.05 molar Tris/HCl is added and the column is allowed to drain.

A 1 ml aliquot of the serum is added to the top of the chromatographic column and the eluate obtained after this addition is collected. Then 1 ml of 0.1 molar sodium chloride, having a pH of 8.0, buffered with 0.05 molar Tris/HCl, is added and the eluate collected with the serum eluate previously collected. This combined eluate (first fraction) comprises the first fraction which contains the hepatic lactic acid dehydrogenase, $LDH_5$, which is assayed in a conventional manner.

Next, 7 ml of 0.1 molar sodium chloride having a pH of 8.0, buffered with 0.05 molar Tris/HCl is passed through the column. Subsequently, in a similar manner, 2 ml of 0.2 molar sodium chloride, having a pH of 8.0, buffered with 0.5 molar Tris/HCl, is passed through the column and the eluate obtained is discarded.

Then, 2 ml of 0.5 molar sodium chloride, having a pH of 7.0, buffered with 0.05 molar Tris/HCl, is passed through the chromatographic column and this eluate is collected. The eluate collected comprises the second fraction and contains simultaneously the diagnostically valuable $LDH_{1,2}$, CPK-MB, and PAP isoenzymes in a single fraction.

The first fraction obtained above is assayed for $LDH_5$ activity and the second fraction obtained above is assayed for $LDH_{1,2}$ and CPK-MB activity using conventional spectrophotometric techniques with the results being reported in International Units. The general formula used for the calculation of International Units is:

$$IU/L = A/T \times T.V./S.V. \times 1/10^{-6}E \times 1000$$

A = Absorbence change between readings
T = Time elapsed between absorbance readings (in minutes)
S.V. = Sample volume (in ml)
T.V. = Total volume (in ml) (Sample plus aqueous buffered salt solution)
E = Molar absorptivity of $NADH_2$ at 340 nm, 6.22 × $10^6$ cm$^2$/mole While normal $LDH_5$ ranges will vary with sex, age, climate, diet, assay procedures, or other factors, in a study of "normal values" from a healthy adult population of 50 individuals a mean ± 1 standard deviation for the $LDH_5$ assay, using the above procedure, was determined to be 16 and 5.7 respectively.

The distribution at 37° C for $LDH_5$ has been found to be nongaussian (See L. E. Nathan et al, *Clin.Chem.*, 19, 1036 (1973)), and if the 0 to 98 percentile range is utilized, the limits of normal for $LDH_5$ was found to be 8 to 26 IU/L at 37° C.

Based on the data of L. E. Nathan et al, supra, a suggested serum $LDH_5$ isoenzyme pattern in indicated diseases is presented in the table below:

| DISEASES ASSOCIATED WITH ELEVATED $LDH_5$ | | | |
|---|---|---|---|
| | Average Times Upper Limit of Normal | Range of Multiple of Upper Limit of Normal | Percentage of Cases Elevated |
| Hepatitis (30) | 18 | 2.3 – 120 | 100 |
| Liver Neoplasms (40) | 11 | 0.4 – 34 | 95 |
| Cirrhosis (10) | 2.3 | 0.2 – 8.2 | 50 |
| Acute Trauma to the Liver (3) | 19 | 2.8 – 48 | 100 |
| Congestive Heart Failure with Hepatic Congestion (11) | 17 | 2.6 – 65 | 100 |
| Muscle Necrosis and | | | |

-continued

| | Average Times Upper Limit of Normal | Range of Multiple of Upper Limit of Normal | Percentage of Cases Elevated |
|---|---|---|---|
| DISEASES ASSOCIATED WITH ELEVATED LDH$_5$ | | | |
| Uremia (9) | 20 | 1.3 – 149 | 100 |

NOTE: The number of samples studied is shown in parenthesis.

Further, the normal ranges of $LDH_{1,2}$ and CPK-MB vary with sex, age, climate, diet, assay procedures, or other factors.

The amount of $LDH_{1,2}$ will generally increase within 24 to 48 hours after myocardial infarction. It has been found that the normal range for $LDH_{1,2}$ is about 8.13 ±4.32 IU/L (mean ± 1 standard deviation) at 37° C and the upper limit of normal is 21 IU/L at 37° C using the above procedures, and when normal values for CPK-MB were determined in a healthy mixed adult population (50), a value of 0.06 ± 0.16 IU/L ± 37° C (mean ± standard deviation) was obtained. However, due to the possibility of the presence of CPK-MB in the serum in non-infarction situations, e.g., myocarditis, and based on clinical experience the following guidelines would appear appropriate:

| Value Obtained (37° C) | Myocardial Infarction Condition Suggested |
|---|---|
| 0–1.0 IU/L | Unlikely |
| 1.1–2.0 IU/L | Borderline value |
| 2.1 or greater IU/L | Yes |

NOTE:
With respect to the "normal values", mean ± 1 standard deviation for total serum LDH and CPK of 96.48 ± 21.26; and 59.88 ± 40.76, respectively IU/L at 37° C was obtained.

EXAMPLE 2

The procedures described in Example 1 are repeated except that 8 ml of a 0.1 molar sodium chloride aqueous solution having a pH of 8, buffered with 0.05 molar Tris/HCl, was employed and all eluates from the column, with the exception of the last eluate obtained on passing the 2 ml of 0.5 molar sodium chloride aqueous solution, was discarded. This fraction can then be analyzed using conventional assay techniques for CPK-MB, $LDH_{1,2}$ and/or PAP for diagnostic use, e.g., as described in Example 1.

While the invention has been described in detail and with respect to specific embodiments thereof, it is apparent that various changes and modifications can be made therein, in accordance with the disclosure contained herein, without departing from the spirit and scope of the invention.

What is claimed is:

1. A process of separating and isolating fractions containing isoenzymes from a sample of tissue extract or blood serum comprising ion-exchange column chromatographically separating said sample containing said isoenzymes into a first fraction containing the hepatic isoenzyme of lactic acid dehydrogenase ($LDH_5$) and a second fraction containing the myocardial isoenzymes of lactic acid dehydrogenase ($LDH_{1,2}$), the myocardial isoenzyme of creatine phosphokinase (CPK-MB) and prostatic acid phophatase by ion-exchange column chromatographing said sample on a weakly-basic anion-exchange chromatographic resin and sequentially eluting and collecting said first fraction and said second fraction, said chromatographing, eluting and collecting being conducted in accordance with the following sequence:

a. passing said sample through the anion-exchange resin in a pre-swelled form in a chromatographic column and collecting a first eluate passing through the column;

b. passing a first aqueous buffered salt solution through the anion-exchange resin in the chromatographic column and collecting a second eluate with said first eluate to obtain said first fraction containing the hepatic isoenzyme of lactic acid dehydrogenase ($LDH_5$), said first aqueous buffered salt solution having a pH of about 7.0 to 8.5, containing a salt with an anion corresponding to the anion of the anion-exchange resin prior to passing said sample, having a concentration in terms of the anion of about 0.01 to 0.15 equivalent/liter and being passed in an amount such that up to about 3 volume equivalents, based on said sample, of said first aqueous buffered salt solution are passed;

c. sequentially passing a second aqueous buffered salt solution and a third aqueous buffered salt solution through the anion-exchange resin in the chromatographic column to obtain a third eluate, said second aqueous buffered salt solution having a pH of about 7.0 to 8.5, containing a salt with an anion corresponding to the anion of the anion-exchange resin prior to the passing of said sample, having a concentration in terms of the anion of about 0.01 to 0.15 equivalent/liter and being passed in an amount such that at least about 4 volume equivalents, based on said sample, of said second aqueous buffered salt solution are passed, and said third aqueous buffered salt solution having a pH of about 7.5 to 8.5, containing a salt with an anion corresponding to the anion of the anion-exchange resin prior to the passing of said sample, having a concentration in terms of the anion of about 0.15 to 0.25 equivalent/liter and being passed in an amount such that about 4 or less volume equivalents, based on said sample, of said third aqueous buffered salt solution are passed; and d. passing a fourth aqueous buffered salt solution through the anion-exchange resin in the chromatographic column and collecting a fourth eluate to obtain said second fraction containing the myocardial isoenzymes of lactic acid dehydrogenase ($LDH_{1,2}$), the myocardial isoenzyme of creatine phosphokinase (CPK-MB) and prostatic acid phosphatase, said fourth aqueous buffered salt solution having a pH of about 6.5 to 7.5, containing a salt with an anion corresponding to the anion of the anion-exchange resin prior to the passing of said sample, having a concentration in terms of the anion of about 0.4 to 0.6 equivalent/liter and being passed in an amount such that about 1 to 6 volume equivalents, based on said sample, of said fourth aqueous buffered salt solution are passed.

2. The process of claim 1, wherein said sample is a sample of blood serum.

3. The process of claim 1, wherein said sample is a tissue extract.

4. The process of claim 1, wherein said anion exchange resin is a diethylaminoethyl dextran anion-exchange resin.

5. The process of claim 1, wherein said anion exchange resin is a diethylaminoethyl cellulose anion-exchange resin.

6. The process of claim 1, wherein said anion exchange resin is a diethylaminoethyl agarose anion-exchange resin.

7. The process of claim 1, wherein said anion exchange resin is a deithylaminoethyl acrylamide anion-exchange resin.

8. The process of claim 1, wherein said process further includes concentrating said first fraction.

9. The process of claim 1, wherein said process further includes concentrating said second fraction.

10. The process of claim 1, wherein said process further includes concentrating said first fraction and said second fraction.

11. The process of claim 5, wherein said first aqueous buffered salt solution is an aqueous buffered alkali metal chloride solution having a pH of about 8, having a concentration in terms of the chloride of about 0.1 equivalent/liter and being passed in an amount such that about 1 volume equivalent, based on said sample, of said first aqueous buffered salt solution is passed; said second aqueous buffered salt solution is an aqueous buffered alkali metal chloride solution having a pH of about 8, having a concentration in terms of the chloride of about 0.1 equivalent/liter and being passed in an amount such that about 7 volume equivalents, based on said sample of said second aqueous buffered salt solution are passed; said third aqueous buffered salt solution is an aqueous buffered alkali metal chloride solution having a pH of about 8, having a concentration in terms of the chloride of about 0.2 equivalent/liter and being passed in an amount such that about 2 volume equivalents, based on said sample, of said third aqueous buffered salt solution, are passed; and said fourth aqueous buffered salt solution is an aqueous buffered alkali metal chloride solution having a pH of about 7, having a concentration in terms of the chloride of about 0.5 equivalent/liter and being passed in an amount such that about 2 volume equivalents of said fourth aqueous buffered salt solution, based on said sample, are passed.

12. The process of claim 11, wherein said alkali metal chloride is sodium chloride.

13. A process for isolating a fraction containing isoenzymes of diagnostic importance in diagnosing heart disorders from a sample of tissue extract or blood serum comprising ion-exchange column chromatographically separating said sample containing said enzymes into a fraction containing the myocardial isoenzymes of lactic acid dehydrogenase ($LDH_{1,2}$), the myocardial isoenzyme of creatine phosphokinase (CPK-MB) and prostatic acid phosphatase by ion-exchange column chromatographing said sample on a weakly-basic anion-exchange chromatographic resin and sequentially eluting and collecting to obtain said fraction containing said myocardial isoenzymes of lactic acid dehydrogenase ($LDH_{1,2}$), said myocardial isoenzyme of creatine phosphokinase (CPK-MB) and said prostatic acid phosphatase, and said chromatographing, eluting and collecting being conducted in accordance with the following sequence:

a. passing said sample through said anion-exchange resin in a pre-swelled form in a chromatographic column and discarding the eluate obtained therefrom;

b. sequentially passing (i) a combination of a first aqueous buffered salt solution and a second aqueous buffered salt solution, and (ii) a third aqueous buffered salt solution through said anion-exchange resin in said chromatographic column to obtain a second eluate and discarding said eluate; said first aqueous buffered salt solution having a pH of about 7.0 to 8.5, containing a salt with an anion corresponding to the anion of said anion-exchange resin prior to passing said sample and having a concentration in terms of said anion of about 0.01 to 0.15 equivalent/liter; said second aqueous buffered salt solution having a pH of about 7.0 to 8.5, containing a salt with an anion corresponding to the anion of said anion-exchange resin prior to said passing of said sample and having a concentration in terms of said anion of about 0.01 to 0.15 equivalent/liter; and the combination being passed in an amount such that at least about 4 volume equivalents based on said sample, of said combination, are passed; and said third aqueous buffered salt solution having a pH of about 7.5 to 8.5, containing a salt with an anion corresponding to the anion of said anion-exchange resin prior to said passing of said sample, having a concentration in terms of said anion of about 0.15 to 0.25 equivalent/liter and being passed in an amount such that about 4 or less volume equivalents, based on said sample, of said third aqueous buffered salt solution, are passed; and c. passing a fourth aqueous buffered salt solution through said anion-exchange resin in said chromatographic column and collecting the eluate to obtain said fraction containing said isoenzymes; said fourth aqueous buffered salt solution having a pH of about 6.5 to 7.5, containing a salt with an anion corresponding to the anion of said anion-exchange resin prior to said passing of said sample, having a concentration in terms of said anion of about 0.4 to 0.6 equivalent/liter and being passed in an amount such that about 1 to 6 volume equivalents, based on said sample, of said fourth aqueous buffered salt solution are passed.

14. The process of claim 13, wherein said sample is a sample of blood serum.

15. The process of claim 13, wherein said sample is a tissue extract.

16. The process of claim 13, wherein said anion-exchange resin is a diethylaminoethyl dextran anion-exchange resin.

17. The process of claim 13, wherein said anion-exchange resin is a diethylaminoethyl cellulose anion-exchange resin.

18. The process of claim 13, wherein said anion-exchange resin is a diethylaminoethyl agarose anion-exchange resin.

19. The process of claim 13, wherein said anion-exchange resin is a diethylaminoethyl acrylamide anion-exchange resin.

20. The process of claim 13, wherein said process further includes concentrating said fraction containing said myocardial isoenzymes of lactic acid dehydrogenase ($LDH_{1,2}$), said myocardial isoenzyme of creatine phosphokinase (CPK-MB) and prostatic acid phosphatase.

21. The process of claim 16, wherein said first aqueous buffered salt solution is an aqueous buffered alkali metal chloride solution having a pH of about 8 and having a concentration in terms of the chloride of about 0.1 equivalent/liter; said second aqueous buffered salt solution is an aqueous buffered alkali metal chloride solution having a pH of about 8, and having a concentration in terms of the chloride of about 0.1 equivalents/liter; and the combination is passed in an amount such that about 8 volume equivalents, based on said sample, of said combination are passed; said third aqueous buffered salt solution is an aqueous buffered alkali metal chloride solution having a pH of about 8, having a concentration in terms of the chloride of about 0.2 equivalent/liter and being passed in an amount such that about 2 volume equivalents, based on said sample, of said third aqueous buffered salt solution are passed; and said fourth aqueous buffered salt solution is an aqueous buffered alkali metal chloride solution having a pH of about 7, having a concentration in terms of the chloride of about 0.5 equivalent/liter and being passed in an amount such that about 2 volume equivalents of said fourth aqueous buffered salt solution, based on said sample, are passed.

22. The process of claim 21, wherein said alkali metal chloride is sodium chloride.

* * * * *

UNITED STATES PATENT AND TRADEMARK OFFICE
CERTIFICATE OF CORRECTION

PATENT NO. : 4,013,513
DATED : March 22, 1977
INVENTOR(S) : William H. Lederer

It is certified that error appears in the above-identified patent and that said Letters Patent are hereby corrected as shown below:

Col. 1, line 53, delete "Chem." and insert therefor -- Chim. --.

Col. 1, line 56, after "$LDH_2$," insert -- $LDH_3$, --.

Col. 2, line 15, delete "Chem." and insert therefor -- Chim. --.

Col. 3, line 8, delete "beind" and insert therefor -- being --.

Col. 16, line 32, delete "absorbence" and insert therefor -- absorbance --.

*Signed and Sealed this*

*Twenty-first* Day of *February 1978*

[SEAL]

Attest:

RUTH C. MASON
*Attesting Officer*

LUTRELLE F. PARKER
*Acting Commissioner of Patents and Trademarks*